United States Patent [19]
Sebag et al.

[11] Patent Number: 5,112,601
[45] Date of Patent: May 12, 1992

[54] ALKYL ESTERS OF N-CARBOALKYLOXY AMINO-11-UNDECANOIC ACIDS, THEIR USE AS THICKENING AGENTS

[75] Inventors: Henri Sebag, Paris; Didier Semeria, Gif sur Yvette, both of France

[73] Assignee: L'Oreal, Paris, France

[21] Appl. No.: 524,783

[22] Filed: May 17, 1990

[30] Foreign Application Priority Data

May 23, 1989 [FR] France ................. 89 06734

[51] Int. Cl.$^5$ ............................................. A61K 7/043
[52] U.S. Cl. .............................. 424/61; 424/DIG. 5; 514/938; 560/160; 560/163
[58] Field of Search ............... 560/160, 163; 260/404; 424/450, 59, 62, 61, DIG. 5; 514/937, 844, 845, 943, 969, 938

[56] References Cited

U.S. PATENT DOCUMENTS

| | | | |
|---|---|---|---|
| 2,401,080 | 5/1946 | Kilgore | 560/160 |
| 3,547,895 | 12/1970 | Vernaleken et al. | 528/328 |
| 3,943,085 | 3/1976 | Kraft | 524/807 |
| 4,094,992 | 6/1978 | Kaplan | 260/404 |
| 4,290,964 | 9/1981 | Reinehr | 260/404 |
| 4,430,505 | 2/1984 | Heitkamper | 560/160 |
| 4,740,600 | 5/1988 | Eian | 560/163 |

FOREIGN PATENT DOCUMENTS

| | | |
|---|---|---|
| 0274756 | 7/1988 | European Pat. Off. |
| 1097431 | 7/1961 | Fed. Rep. of Germany |
| 3328455 | 3/1985 | Fed. Rep. of Germany |
| 1551661 | 12/1968 | France |

OTHER PUBLICATIONS

Chemical Abstracts, vol. 102, Mar. 18, 1985, No. 11, p. 546.
R. Harry, "Stick Make-up", Harry's Cosmeticology (1982), pp. 311-312.
R. Harry, "Cleansing (Complexion) Milks and Liquid Creams", Modern Cosmeticology (vol. 1, 1962), pp. 89-91.

Primary Examiner—Thurman K. Page
Assistant Examiner—D. Colucci
Attorney, Agent, or Firm—Oliff & Berridge

[57] ABSTRACT

The alkyl esters of N-carboalkyloxy-11-aminoundecanoic acids have the following general formula:

$$R'-O-\overset{O}{\overset{\|}{C}}-NH-(CH_2)_{10}-\overset{O}{\overset{\|}{C}}-OR \quad (1)$$

wherein R is linear or branched $C_{7-30}$ alkyl, linear or branched $C_{4-22}$ alkenyl or a radical of formula:

$$-(CH_2)_n-\underset{}{\underset{}{\bigcirc}}-R''$$

wherein
n is 0 to 5
R'' is H or linear or branched $C_{1-9}$ alkyl, and
R' is linear $C_{10-18}$ alkyl.

These esters, and esters wherein R is additionally hydrogen or $C_{1-6}$, have an application as thickening agents in organic media particularly in the cosmetic field.

7 Claims, No Drawings

ALKYL ESTERS OF N-CARBOALKYLOXY AMINO-11-UNDECANOIC ACIDS, THEIR USE AS THICKENING AGENTS

BACKGROUND OF THE INVENTION (i) Field of the invention

This invention relates to new alkyl esters of N-carboalkyloxy amino-11-undecanoic acids and to their processes of preparation and their use as thickening agents particularly in organic media. The new compounds have applications particularly in the thickening and/or solidification of oily liquids and organic solvents such as may be used for example in cosmetics, pharmacy, paints and varnishes, lubricants, fuels as well as in the food industry. These compounds have proved by their properties to be the thickeners of choice for a large number of cosmetic compositions particularly nail varnish.

(ii) Description of the Prior Art

Current thickeners for non-aqueous milieux include N-acylaminoacids, salts of fatty acids, e.g., aluminum aluminium, magnesium or calcium salts, glycerol esters of fatty acids, inorganic colloids such as bentone, as well as natural products like beeswax or even carnauba wax.

OBJECTS OF THE INVENTION

It is an object of the present invention to provide thickening agents of non-ionic character or very slightly ionic in character. It is a further object of this invention to provide thickeners able to mix with a variety of other adjuvants such as, for example, surfactants, polymers, preservatives, colourants, pigments, perfumes and a variety of active compounds.

SUMMARY OF THE INVENTION

The invention provides alkyl esters of N-carboalkyloxy amino-11-undecanoic acids of general formula :

$$R'-O-\overset{O}{\underset{\|}{C}}-NH-(CH_2)_{10}-\overset{O}{\underset{\|}{C}}-OR \quad (I)$$

in which :

R is linear or branched $C_{7-30}$ alkyl, linear or branched $C_{4-22}$ alkenyl or a radical of formula :

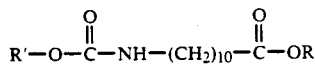

in which:
n is 0 to 5
R" is H, linear or branched $C_{1-9}$ alkyl, and
R' is linear $C_{10-18}$ alkyl.

DESCRIPTION OF PREFERRED EMBODIMENTS

When R is linear or branched $C_{7-30}$ alkyl, it is preferably octyl, dodecyl, tetradecyl, hexadecyl, octadecyl, hexyl-2-decyl, isostearyl, docosyl or triacontyl.

When R is linear or branched $C_{7-22}$ alkenyl, it is preferably undecen-10-yl, octadecen-9-yl (=oleyl) or docosen-13-yl (erucyl).

When R is

When R is $-(CH_2)_n-$ 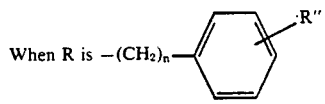

it is preferably benzyl, phenethyl, p-xylyl or nonylphenyl. R' is preferably dodecyl, tetradecyl, hexadecyl or octadecyl but in particular, hexadecyl.

According to one embodiment of the invention, R is linear or branched $C_{14-20}$ alkyl.

It has been discovered in a wholly surprising and unexpected manner that these alkyl esters of N-carboalkyloxy amino-11-undecanoic acids possess excellent thixotropic properties which are particularly interesting and sought after for varnishes, especially nail varnish.

Among the compounds covered by general formula I above the following are worth mentioning :

octyl N-carbohexadecyloxy amino-11-undecanoate,
dodecyl N-carbohexadecyloxy amino-11-undecanoate,
tetradecyl N-carbohexadecyloxy amino-11-undecanoate,
hexadecyl N-carbohexadecyloxy amino-11-undecanoate,
octadecyl N-carbohexadecyloxy amino-11-undecanoate,
docosyl N-carbohexadecyloxy amino-11-undecanoate,
triacontyl N-carbohexadecyloxy amino-11-undecanoate,
oleyl N-carbohexadecyloxy amino-11-undecanoate,
isostearyl N-carbohexadecyloxy amino-11-undecanoate,
benzyl N-carbohexadecyloxy amino-11-undecanoate, and
hexadecyl N-carbodecyloxy amino-11-undecanoate.

The present invention also relates to the process for preparing the above defined N-carboalkyloxy amino-11-undecanoic acid esters. Various methods may be employed for the synthesis of these compounds. One such comprises reacting a fatty alcohol (R'-OH) with an isocyanate of formula : $O=C=N-(CH_2)_{10}-CO-OR$ (II), R and R' being as defined above for formula I. Another method comprises reacting a chloroformiate of formula R'OCOCl or an azolide of formula :

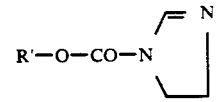

with an amine of formula $H_2N-(CH_2)_{10}-CO-OR$ (III), R and R' being as defined above.

These two methods, which aim to produce the carbamate function, may be carried out according to conventional methods, such as are described in particular in "Advanced Organic Chemistry" Third Edition, Ed. Jerry, March 1985, incorporated herein by reference. The reactions are generally conducted in organic and/or aqueous solvent(s) in the presence of a base which is preferably caustic soda, caustic potash or triethylamine.

These methods may also be carried out starting from the acids of compounds II and III (ie where R=H) in which case the esters are obtained by classical methods notably by esterification in the presence of the chosen alcohol (optionally in excess) and of an acidic catalyst such as sulphuric acid or paratoluene sulphonic acid optionally in an organic solvent, preferably an aromatic solvent such as toluene.

Again starting from the salts of these acids, it is possible to produce the esters by classical methods, notably by substitution using halide compounds or alkoyl sulphonates, in organic solvent(s) or by phase transfer.

It is also possible to obtain the claimed esters by transesterification starting from methyl and ethyl esters and the desired alcohol. The present invention also relates to the use of the compounds of formula I according to the invention, wherein R may additionally be H or $C_1$ to $C_6$, as thickening agents of certain solvents, oils, paints and varnishes, cosmetic compositions, particularly nail varnish, and pharmaceutical compositions.

Representative animal, vegetable or mineral oils which may be thickened using the compounds of the invention include vaseline, colza oil, olive oil, jojoba oil, perhydrosqualene as well as silicone oils and esters of fatty acids.

Representative solvents include hydrocarbons such as xylene, toluene, heptane, isooctane, esters such as butyl acetate, isopropyl myristate, ketones such as methylisobutylketone, acetone, chlorinated hydrocarbons such as 1,2-dichloroethane, glycol ethers such as polyethylene glycol, 2-butoxyethanol, alcohols such as ethanol, isopropanol, 2-ethylhexanol, polyoxyethenated alkoylphenols etc.

The thickening of these media is effected by dissolution therein of all the thickening agent and thereafter putting the mixture aside until it has completely thickened. It is possible to achieve a homogenous mixture at temperatures between ambient and the boiling point of the organic liquid followed by cooling the solution thus obtained.

The proportion of thickening agent according to the invention may vary within a broad range depending on the medium to be thickened but lies generally between 0.1 and 25 % by weight referred to the total weight of the medium.

In the case of cosmetic and pharmaceutical compositions, the porportion of thickening agents lies generally between 0.1 and 15% by weight referred to the total weight of the composition. Here, various formulations are possible such as for example water-in-oil emulsions, oil-in-water emulsions, sticks, milks, etc. The compounds of formula I according to the invention where R is linear or branched $C_{14-20}$ alkyl have application as thixotropic thickeners in nail varnish. In this particular embodiment, they are generally present in a proportion between 0.2 and 7% by weight related to the total weight of the nail varnish.

There now follows for the purposes of illustration and without any intent to limit the scope of the present invention, several examples of preparing N-carboalkyloxy amino-11-undecanoic acid esters as well as several examples of the use of these compounds as thickening agents.

EXAMPLE A

Preparation of N-carbohexadecyloxy-11-aminoundecanoic acid 40.2 g of 11-amino-undecanoic acid (0.2 mol) are dissolved in a mixture of 450 ml acetone and 200 ml of 1N caustic soda. Simultaneously 60.9 g (0.2 mol) of hexadecyl chloroformate are added along with 200ml of a 1N caustic soda solution. A white precipitate progressively appears in the reaction medium which is continuously agitated for 5 hours. Thereafter, the reaction medium is filtered and the white precipitate obtained is washed with water. The alkaline salt obtained is filtered under vacuum then dissolved and acidified in 650 ml of hot acetic acid. Reducing to ambient temperature leads to the appearance of a white precipitate which is filtered and washed with acetone. The acid thus obtained is dried under vacuum at 40° C. to constant weight of no less that 79 g (minimum yield : 85%) having a melting point of 100° C.±1° C.

The 13-C NMR spectrum corresponds to the expected structure. IR spectrum : 1538cm-1 and 1679cm-1 (carbamate).

| | Quantitative analysis of $C_{28}H_{55}NO_4$ | | | |
|---|---|---|---|---|
| | C % | H % | N % | O % |
| Calculated: | 71.59 | 11.80 | 2.98 | 13.62 |
| Found: | 71.40 | 11.84 | 2.93 | 13.68 |

EXAMPLE B

Preparation of N-carbodecyloxy-11-aminoundecanoic acid

Using the same procedure as in example A, and using 44.1 g of decyl chloroformiate, 61 g of white crystals are obtained (yield=80%) having a melting point of 91° C. The 1-H NMR spectrum accords with the expected structure. IR spectrum : 1679cm-1 and 1535cm-1 (carbamate)

EXAMPLE 1

Preparation of octyl N-carbohexadecyloxy-11-aminoundecanoate 1.5 g octanol, 300mg paratoluene sulphonic acid and 120 ml toluene are added to 5 g of the acid obtained in example A. Dehydration is carried out by azeotropic entrainment for 16 hours after which the reaction medium is evaporated to dryness under vacuum. The white precipitate obtained is subjected to chromatography on a silica column and methylene chloride as eluant. After evaporation of the elution solvent under vacuum, 5 g of pure white crystals are recovered (yield =80%) having a melting point of 66° C.

The 13C and 1-H NMR spectra were as expected for the structure. IR spectrum : 1730cm-1 (ester) 1685cm-1 and 1535cm-1 (carbamate)

| | Quantitative analysis: $C_{36}H_{71}NO_4$ | | | |
|---|---|---|---|---|
| | C % | H % | N % | O % |
| Calculated: | 74.30 | 12.30 | 2.41 | 11.00 |
| Found: | 74.45 | 12.33 | 2.46 | 10.95 |

EXAMPLE 2

Preparation of dodecyl N-carbohexadecyloxy-11-aminoundecanoate

Using the same procedure as in example 1 and using 2.g of lauryl, alcohol, 5.4 g of pure white crystals are obtained (yield=80%) having a melting point of 69°-70° C.

The 1-H NMR spectrum (250 MHz) corresponds with the expected structure.

IR spectrum : 1726cm-1 (ester) 1685cm-1 and 1551cm-1 (carbamate)

| Quantitative analysis: $C_{40}H_{79}NO_4$ | | | | |
|---|---|---|---|---|
| | C % | H % | N % | O % |
| Calculated | 75.29 | 12.48 | 2.20 | 10.03 |
| Found | 75.22 | 12.51 | 2.27 | 10.18 |

EXAMPLE 3

Preparation of tetradecyl N-carbohexadecyloxy-11-aminoundecanoate

Using the same procedure as in example of tetradecanol, 5.6 g of pure white crystals are obtained (yield = 80%) having a melting point of 73° C. The 1-H NMR spectrum (250MHz) corresponds with the expected structure. IR spectrum : 1727cm-1 (ester) 1686cm-1 and 1537cm-1 (carbamate)

| Quantitative analysis: $C_{42}H_{83}NO_4$ | | | | |
|---|---|---|---|---|
| | C % | H % | N % | O % |
| Calculated | 75.73 | 12.56 | 2.10 | 9.61 |
| Found | 75.88 | 12.61 | 2.06 | 9.63 |

EXAMPLE 4

Preparation of hexadecyl N-carbohexadecyloxy-11-aminoundecanoate (i) Following the same procedure as that described in example 1 and using 2.7 g of hexadecanol, 5.9 g of pure white crystals are obtained (yield = 80%) having a melting point of 76° C.

The 13-C NMR spectrum corresponds to the expected structure.

IR spectrum : 1730cm-1 (ester) 1685cm-1 and 1536cm-1 (carbamate)

| Quantitative analysis $C_{44}H_{87}NO_4$ | | | | |
|---|---|---|---|---|
| | C % | H % | N % | O % |
| Calculated: | 76.13 | 12.63 | 2.02 | 9.22 |
| Found: | 75.55 | 12.75 | 2.06 | 9.76 |

(ii) 3.4 g of 1-bromohexadecane in 100 ml acetonitrile are added to 5 g of the sodium carboxylate obtained as intermediate in example A. After having refluxed for 8 hours, the reaction medium is evaporated to dryness.

The white precipitate is subjected to chromatography on a silica column using methylene chloride as eluant.

After evaporation of the elution solvent under vacuum, 4.6 g (yield 65%) of pure white crystals are obtained, identical to those in (1) above.

EXAMPLE 5

Preparation of octadecyl N-carbohexadecyl-11-amino undecanoate

Following the procedure of example 1 and using 3.1 g of octadecanol, 6.1 g of pure white crystals (yield = 80%) are obtained having a melting point of 78° C. The 1-H NMR spectrum (250 MHz) corresponds to the expected structure.

IR spectrum : 1726cm-1 (ester) 1686cm-1 and 1536cm-1 (carbamate)

| Quantitative analysis $C_{46}H_{91}NO_4$ | | | | |
|---|---|---|---|---|
| | C % | H % | N % | O % |
| Calculated: | 76.50 | 12.70 | 1.94 | 8.86 |
| Found: | 76.57 | 12.69 | 2.01 | 8.89 |

EXAMPLE 6

Preparation of docosyl N-carbohexadecyloxy-11-aminoundecanoate

Following the procedure of example 1 and using 3.6 g of docosanol, 6.6 g of pure white crystals (yield = 80%) are obtained having a melting point of 81°-82° C.

The 1-H NMR spectrum (250 MHz) corresponds to the expected structure.

IR spectrum : 1726cm-1 (ester) 1685cm-1 and 1536cm-1 (carbamate)

| Quantitative analysis $C_{50}H_{99}NO_4$ | | | | |
|---|---|---|---|---|
| | C % | H % | N % | O % |
| Calculated: | 77.16 | 12.82 | 1.80 | 8.22 |
| Found: | 77.19 | 12.85 | 1.79 | 8.13 |

EXAMPLE 7

Preparation of triacontyle N-carbohexadecyloxy-llaminoundecanoate

Following the same procedure as in example 1, and using 4.90 g of triacontanol ("Unilin TM 425" by PETROLITE), 4.7 g of waxy crystals (50% yield) are obtained having a melting point of 69.5°-71° C. The 13-C NMR spectrum corresponds to the expected structure.

IR spectrum : 1727cm-1 (ester) 1686cm-1 and 1537cm-1 (carbamate)

EXAMPLE 8

Preparation of oleyl N-carbohexadecyloxy-11-aminoundecanoate

Following the same procedure as in example 1 and using 3.0 g of oleyl alcohol, 6.1 g of pure white crystals (80% yield) are obtained having a melting point of 62° C.

The 1-H NMR spectra (250 MHz) correspond to the expected structure.

IR spectrum : 1726cm-1 (ester) 1685cm-1 and 1551cm-1 (carbamate)

| Quantitative analysis $C_{46}H_{89}NO_4$ | | | | |
|---|---|---|---|---|
| | C % | H % | N % | O % |
| Calculated: | 76.71 | 12.46 | 1.94 | 8.89 |
| Found: | 76.83 | 12.37 | 1.96 | 8.66 |

EXAMPLE 9

Preparation of isostearyl N-carbohexadecyloxy-11-aminoundecanoate

Following the procedure of example 1, and using 3.0 g isostearyl alcohol (REWO TM Aldol 66) 6.1g of white crystals (80% yield) are obtained having a melting point of 68°±2° C. The 13-C and 1-H NMR spectra (250 MHz) correspond to the expected structure.

IR spectrum : 1728cm-1 (ester) 1686cm-1 and 1537cm-1 (carbamate)

| Quantitative analysis: C<sub>40</sub>H<sub>91</sub>NO<sub>4</sub> | | | |
|---|---|---|---|
| | C % | H % | N % | O % |
| Calculated | 76.50 | 12.70 | 1.94 | 8.86 |
| Found | 76.60 | 12.82 | 1.98 | 9.10 |

EXAMPLE 10

Preparation of benzyle N-carbohexadecyloxy-11-aminoundecanoate

Following the procedure of example 1, and using 1.2 g of benzyl alcohol, 4.8 g of pure white crystals (80% yield) are obtained having a melting point of 71°–72° C.

The 1-H NMR spectrum (250 MHz) corresponds to the expected structure.

IR spectrum : 1734cm-1 (ester) 1684cm-1 and 1529cm-1 (carbamate)

| Quantitative analysis C<sub>35</sub>H<sub>61</sub>NO<sub>4</sub> | | | |
|---|---|---|---|
| | C % | H % | N % | O % |
| Calculated: | 75.08 | 10.98 | 2.50 | 11.43 |
| Found: | 75.23 | 10.95 | 2.49 | 11.64 |

EXAMPLE 11

Preparation of hexadecyl N-carbodecyloxy-11-aminoundecanoate 3.3 g of hexadecanol, 300mg of paratoluene sulphonic acid and 80 ml of toluene are added to 5 g of the acid obtained in example B. Dehydration is carried out by azeotropic entrainment for 16 hours, after which the reaction mixture is evaporated to dryness under vacuum.

The white precipitate obtained is subjected to chromatography on a silica column using methylene chloride as eluant. After evaporation of the elution solvent under vacuum, 6.3 g of pure white crystals (80% yield) are recovered having a melting point of 65° C.

The 1-H NMR spectrum corresponds to the expected structure.

IR spectrum : 1725cm-1 (ester) 1635cm-1 and 1685cm-1 (carbamate)

Examples of Formulation

EXAMPLE A

Lipstick

| | |
|---|---|
| Ricin oil | 72.5% |
| Hexadecyl N-carbohexadecyloxy-11-aminoundecanoate | 15% |
| Mica-titanium | 7% |
| Talc q.s.p. | 3% |
| Titanium dioxide q.s.p. | 2.5% |
| Pigments q.s. | |
| Perfume q.s. | |

Example B

Stick

| | |
|---|---|
| Codex cocoa butter | 10% |
| Ozokerite | 24% |
| Refined white paraffin | 4% |
| Codex ricin oil | 8% |
| Oleyl alcohol | 6% |
| Clear odourless lanolin | 8% |
| 2-ethyl hexyl-p-methoxycinnamate | 2% |
| BHT (butyl hydroxytoluene) | 0.025% |
| BHA (butyl hydroxy anisole) | 0.025% |
| hexadecyl N-carbohexadecyloxy-11-aminoundecanoate | 1% |
| Perfume | 0.8% |
| Vaseline oil q.s.p. | 100% |

EXAMPLE C

Anhydrous nail varnish

| | |
|---|---|
| Copolymer of butyl methacrylate (70%) and hydroxypropyl methacrylate (30%) | 24% |
| Tributyl acetylcitrate | 4% |
| Butyl acetate | 22.8% |
| Ethyl acetate | 9.8% |
| Toluene | 32.7% |
| Ethanol | 5.7% |
| Octadecyl N-carbohexadecyloxy-11-aminoundecanoate | 1% |

EXAMPLE D

Anhydrous nail varnish

| | |
|---|---|
| Copolymer of butyl methacrylate (50%) and Hydroxypropyl methacrylate (50%) | 30% |
| Tributyl acetylcitrate | 7% |
| Butyl acetate | 20.2% |
| Ethyl acetate | 8.6% |
| Toluene | 28.9% |
| Ethanol | 5% |
| Hexadecyl N-carbohexadecyloxy-11-aminoundecanoate | 0.3% |

EXAMPLE E

Sun Cream, Water-in-Oil

| | |
|---|---|
| Octyl dodecanol | 10% |
| Magnesium stearate | 4% |
| Natural beeswax | 5% |
| Hydrogenated lanolin | 1% |
| Clear odourless lanolin | 4% |
| Sorbitan sesquioleate | 4.5% |
| Glycerol mono and distearate and potassium stearate | 1% |
| Vaseline oil | 22% |
| 2-ethyl hexyl p-methoxycinnamate | 5% |
| Hexadecyl N-carbohexadecyloxy-11-aminoundecanoate | 1% |
| Preservatives | 0,4% |
| Perfume | 0,6% |
| Water q.s.p. | 100% |

EXAMPLE F

Protective handcream

| | |
|---|---|
| Mono- and diglyceride of isostearic acid esterified by succinic acid | 5% |
| Vaseline oil | 8% |
| White vaseline | 5% |
| Capric and caprylic triglycerides | 12.3% |
| *****N-carbohexadecyloxy-11-aminoundecanoic acid | 2% |
| Magnesium sulphate | 2% |
| Glycerine | 3% |
| Preservatives | 0.4% |
| Water q.s.p. | 100% |

Epprecht viscosity at 25° C.=3 Pa.S

EXAMPLE G

Night renewal cream

| | |
|---|---|
| Mono- and diglyceride of isostearic acid esterified with succinic acid | 5% |
| Vaseline oil | 8% |
| White vaseline | 5% |
| Capric and caprylic triglycerides | 12.3% |
| Hexadecyl N-carbohexadecyloxy-11-aminoundecanoate | 2% |
| Magnesium sulphate | 2% |
| Glycerine | 3% |
| Preservatives | 0.4% |
| Water | 100% |

Epprecht viscosity at 25° C.=4.3 Pa.S

EXAMPLE H

Body milk

| | |
|---|---|
| Ethers of dodecanediol (22 mol) and of polyethyleneglycol (450E) | 2% |
| β-hydroxyoctacosanyl 12-hydroxystearate | 1% |
| Polyglyceryl-2 sesquioleate | 6% |
| Vaseline oil | 10.7% |
| Volatile silicone oil | 10.7% |
| Capric and caprylic triglycerides | 4% |
| Hexadecyl N-carbohexadecyloxy-11-aminoundecanoate | 1% |
| Magnesium sulphate | 2% |
| Glycerine | 3% |
| Preservatives | 0.4% |
| Water q.s.p. | 100% |

Epprecht viscosity at 25° C.=0.8 Pa.S

EXAMPLE I

Body milk

| | |
|---|---|
| Ethers of dodecanediol (22 mol) and of polyethyleneglycol (450E) | 2% |
| β-hydroxyoctacosanyl 12-hydroxystearate | 1% |
| Polyglyceryl-2 sesquioleate | 6% |
| Vaseline oil | 10.7% |
| Volatile silicone oil | 10.7% |
| Capric and caprylic triglycerides | 4% |
| *****N-carbohexadecyloxy-11-aminoundecanoic acid | 1% |
| Magnesium sulphate | 2% |
| Glycerine | 3% |
| Preservatives | 0.4% |
| Water q.s.p. | 100% |

Epprecht viscosity at 25° C.: 0.6 Pa.S

EXAMPLE J

Light facial cream

| | |
|---|---|
| Ethers of dodecanediol (22 mol) and of polyethyleneglycol (450E) | 2% |
| β-hydroxyoctacosanyl 12-hydroxystearate | 1% |
| Polyglyceryl-2 sesquioleate | 6% |
| Solid purcellin | 4% |
| Mixture of triglycerides of cocoa fatty acids ($C_8$-$C_{18}$) | 3.5% |
| Light vaseline oil | 6.5% |
| Capric and caprylic tryglycerides | 5% |
| Volatile silicone oil | 6% |
| Hexadecyl N-carbohexadecyloxy-11-aminoundecanoate | 2% |
| Magnesium sulphate | 2% |
| Glycerine | 3% |
| Preservatives | 0.4% |
| Water q.s.p. | 100% |

Epprecht viscosity at 25° C.: 1.4 Pa.S.

EXAMPLE K

Protective day cream

| | |
|---|---|
| Copolymers of dodecylglycol/methoxy polyethyleneglycol (220E) | 3.2% |
| β-hydroxyoctacosanyl 12-hydroxystearate | 0.5% |
| Polyglyceryl-2 sesquioleate | 4.8% |
| Vaseline oil | 11% |
| Volatile silicone oil | 8% |
| Capric and caprylic triglycerides | 4% |
| *****N-carbohexadecyloxy-11-aminoundecanoic acid | 2% |
| Magnesium sulphate | 2% |
| Glycerine | 3% |
| Preservatives | 0.4% |
| Water q.s.p. | 100% |

Epprecht viscosity at 25° C.: 2 Pa.S.

EXAMPLE L

Liquid moisturizing emulsion

| | |
|---|---|
| Copolymers of dodecylglycol/methoxy polyethyleneglycol (220E) | 3.2% |
| β-hydroxyoctacosanyl 12-hydroxystearate | 0.5% |
| Polyglyceryl-2 sesquioleate | 4.8% |
| Squalane | 11% |
| Volatile silicone oil | 9% |
| Jojoba oil | 4% |
| Hexadecyl N-carbohexadecyloxy 11-aminoundecanoate | 1% |
| Magnesium sulphate | 2% |
| Glycerine | 3% |
| Preservatives | 0.4% |
| Water q.s.p. | 100% |

Epprecht viscosity at 25° C.: 0.65 Pa.S.

EXAMPLE M

Oil-in-water cream

| | |
|---|---|
| Ketostearyl alcohol and oxyethylenated fatty alcohols | 7% |
| Mixture of non-autoemulsionable glyerol mono- and distearate | 2% |
| Cetyl alcohol | 0.5% |
| Hexadecyl N-carbohexadecyloxy-11-aminoundecanoate | 1% |
| Silicone oil | 1.5% |
| Vaseline oil | 15% |
| 2-ethyl-hexyl-p-methoxycinnamate | 5% |
| Propyleneglycol | 20% |
| Preservatives | 0.4% |
| Perfume | 0.6% |
| Water q.s.p. | 100% |

EXAMPLE N

Water-in-oil cream

| | |
|---|---|
| Octyl dodecanol | 10% |
| Magnesium stearate | 4% |
| Natural beeswax | 5% |
| Hydrogenated lanolin | 1% |
| Clear odourless lanolin | 4% |
| Sorbitan sesquioleate | 4.5% |
| Glycerol mono and distearate and potassium stearate | 1% |
| Vaseline oil | 22% |
| 2-ethyl-hexyl-p-methoxycinnamate | 5% |
| Hexadecyl-N-carbodecyloxy-11-aminoundecanoate | 1% |
| Preservatives | 0.4% |
| Perfume | 0.6% |
| Water q.s.p. | 100% |

EXAMPLE O

Oil-in-water cream

| | |
|---|---|
| Glycerol monostearate | 6% |
| Pure stearyl alcohol | 4% |
| Vaseline oil | 10% |
| 2-methyl-hexyl-p-methoxycinnamate | 4% |
| Silicone oil | 1.5% |
| Octyl-N-carbohexadecyloxy-11-aminoundecanoate | 1% |
| Pure codex glycerine | 20% |
| Preservatives | 0.4% |
| Perfume | 0.6% |
| Water q.s.p. | 100% |

We claim:

1. A composition comprising a liquid organic medium which comprises an oily liquid selected from the group consisting of animal, vegetable and mineral oils or a solvent selected from the group consisting of hydrocarbons, chlorinated hydrocarbons, esters, alcohols, ketones and glycol ethers, and a thickening agent which comprises an alkyl ester of N-carboalkyloxy-11-amino undecanoic acid of general formula:

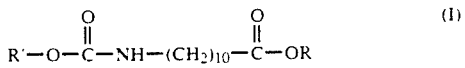

in which:

R is H or is linear or branched $C_1$-$C_{30}$ alkyl, linear or branched $C_4$-$C_{22}$ alkenyl or a radical of formula:

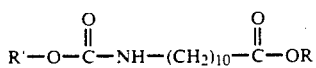

in which n is 0 to 5;

R'' is hydrogen or linear or branched $C_1$-$C_9$ alkyl; and

R' is linear $C_{10}$-$C_{18}$ alkyl.

2. A composition according to claim 1, wherein that the thickening agent is present in an amount between 0.1 and 25% and preferably between 0.1 and 15% of the total weight of the composition.

3. A composition according to claim 1, wherein it is in the form of an oil-in-water emulsion, a water-in-oil emulsion, a solid stick or a milk.

4. Nail varnish, comprising a liquid organic medium which comprises an oily liquid selected from the group consisting of animal, vegetable and mineral oils or a solvent selected from the group consisting of hydrocarbons, chlorinated hydrocarbons, esters, alcohols, ketones and glycol ethers, and a thickening agent which comprises an alkyl ester of N-carboalkyloxy-11-amino undecanoic acid of general formula:

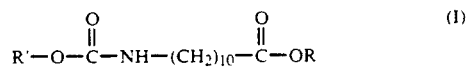

in which:

R is linear or branched $C_{14}$-$C_{20}$ alkyl; and

R' is linear $C_{10}$-$C_{18}$ alkyl.

5. Nail varnish according to claim 4, wherein the thixotropic thickening agent is present in an amount between 0.2 and 7% by weight of to the total weight of the varnish.

6. A process of thickening organic media comprising oily liquids or organic solvents used in cosmetics, pharmaceuticals, paints, varnishes, lubricants, fuels or in the food industry, wherein said oily liquids are selected from the group consisting of animal, vegetable and mineral oils and said solvents are selected from the group consisting of hydrocarbons, chlorinated hydrocarbons, esters, alcohols, ketones and glycol ethers, comprising mixing with said oily liquids or organic solvents a thickening effect amount of any alkyl ester of N-carboalkyloxy-11-amino undecanoic acid of general formula:

$$R'-O-\overset{O}{\underset{\|}{C}}-NH-(CH_2)_{10}-\overset{O}{\underset{\|}{C}}-OR \qquad (I)$$

in which:

R is H or is linear or branched $C_1$-$C_{30}$ alkyl, linear or branched $C_4$-$C_{22}$ alkenyl or a radical of formula:

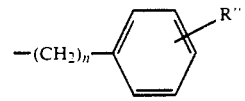

in which n is 0 to 5;

R'' is hydrogen or linear or branched $C_1$-$C_9$ alkyl; and

R' is linear $C_{10}$-$C_{18}$ alkyl.

7. The process according to claim 6, wherein the alkyl ester compounds are used in an amount between 0.1 and 25% by weight of the oily liquids or organic solvents.

* * * * *